(12) United States Patent
Liu (10) Patent No.: US 9,955,728 B2
(45) Date of Patent: May 1, 2018

(54) BATTERY ASSEMBLY AND ATOMIZING ASSEMBLY OF ELECTRONIC CIGARETTE AND ELECTRONIC CIGARETTE

(71) Applicant: KIMREE HI-TECH INC., Tortola (VG)

(72) Inventor: Qiuming Liu, Shenzhen (CN)

(73) Assignee: HUIZHOU KIMREE TECHNOLOGY CO., LTD. SHENZHEN BRANCH, Guangdong (CN)

( * ) Notice: Subject to any disclaimer, the term of this patent is extended or adjusted under 35 U.S.C. 154(b) by 0 days. days.

(21) Appl. No.: 14/361,713

(22) PCT Filed: Dec. 30, 2013

(86) PCT No.: PCT/CN2013/090901
§ 371 (c)(1),
(2) Date: May 30, 2014

(87) PCT Pub. No.: WO2015/078084
PCT Pub. Date: Jun. 4, 2015

(65) Prior Publication Data
US 2016/0309779 A1   Oct. 27, 2016

(30) Foreign Application Priority Data
Nov. 28, 2013   (CN) ...................... 2013 2 0772413 U (51) Int. Cl.
*A24F 47/00*   (2006.01)
*H02J 7/00*   (2006.01)
(Continued)

(52) U.S. Cl.
CPC ......... *A24F 47/008* (2013.01); *H05B 1/0297* (2013.01); *G01N 21/84* (2013.01);
(Continued)

(58) Field of Classification Search
None
See application file for complete search history.

(56) References Cited

U.S. PATENT DOCUMENTS 5,530,225 A * 6/1996 Hajaligol .............. A24F 47/008
131/194
5,665,262 A * 9/1997 Hajaligol .............. A24F 47/008
131/194
(Continued)

FOREIGN PATENT DOCUMENTS

| CN | 101366554 A | 2/2009 |
|---|---|---|
| CN | 202890466 U | 4/2013 |

(Continued)

OTHER PUBLICATIONS

International Search Report from corresponding PCT/CN2013/090901 dated Sep. 9, 2014, 8 pages.
(Continued)

*Primary Examiner* — Joseph M Pelham
(74) *Attorney, Agent, or Firm* — Ohlandt, Greeley, Ruggiero & Perle, LLP (57) ABSTRACT

A battery assembly of an electronic cigarette according to the present application is configured to form an electronic cigarette in combination with an atomizing assembly. The atomizing assembly is provided with a gas storage chamber configured to store cigarette-liquid odor to be detected. The battery assembly includes a sensor group and a microcontroller. After the sensor group detects the cigarette-liquid odor to be detected, the microcontroller is configured to control a circuit between the battery assembly and the atomizing assembly to be switched on in a case that the cigarette-liquid odor to be detected matches the preset odor information, to enable the electronic cigarette to work normally. Thus, the electronic cigarette has an identification
(Continued)

function and can be normally used only when the battery assembly and the atomizing assembly of the electronic cigarette are matched.

20 Claims, 8 Drawing Sheets (51) Int. Cl.
 *H05B 1/02* (2006.01)
 *H01M 2/00* (2006.01)
 *G01N 21/84* (2006.01)
 *H01M 2/10* (2006.01)

(52) U.S. Cl.
 CPC .......... *H01M 2/1022* (2013.01); *H02J 7/0063* (2013.01); *H02J 2007/0001* (2013.01); *H05B 1/02* (2013.01)

(56) References Cited

U.S. PATENT DOCUMENTS

| | | | | |
|---|---|---|---|---|
| 5,878,752 | A * | 3/1999 | Adams | A24F 47/008 131/194 |
| 5,967,148 | A * | 10/1999 | Harris | A24F 47/008 131/329 |
| 9,820,509 | B2 * | 11/2017 | Newton | H05B 1/0244 |
| 2009/0095312 | A1 * | 4/2009 | Herbrich | A61M 11/041 131/273 |
| 2011/0181421 | A1 * | 7/2011 | Nabata | A24F 47/00 340/573.1 |
| 2011/0254444 | A1 * | 10/2011 | Yeulash | H05H 1/2406 315/70 |
| 2013/0213418 | A1 * | 8/2013 | Tucker | A24F 47/008 131/328 |
| 2013/0220315 | A1 * | 8/2013 | Conley | A24F 47/008 128/202.21 |
| 2013/0228191 | A1 * | 9/2013 | Newton | A61M 15/06 131/329 |
| 2013/0263869 | A1 * | 10/2013 | Zhu | A24F 47/002 131/329 |
| 2014/0123989 | A1 * | 5/2014 | LaMothe | A24F 47/008 131/328 |
| 2014/0151363 | A1 * | 6/2014 | Gros D'Aillon | G21C 17/001 219/534 |
| 2014/0299138 | A1 * | 10/2014 | Xiang | A24F 47/008 131/329 |
| 2015/0075545 | A1 * | 3/2015 | Xiang | A24F 47/008 131/329 |
| 2015/0101625 | A1 * | 4/2015 | Newton | H05B 1/0244 131/329 |
| 2015/0189695 | A1 * | 7/2015 | Xiang | G06K 7/10861 219/209 |
| 2015/0208731 | A1 * | 7/2015 | Malamud | H05B 1/0244 131/328 |
| 2015/0224268 | A1 * | 8/2015 | Henry | A24F 47/008 128/202.21 |
| 2015/0258289 | A1 * | 9/2015 | Henry, Jr. | A61M 15/06 128/202.21 |
| 2016/0029698 | A1 * | 2/2016 | Xiang | H04B 5/0025 131/328 |
| 2016/0278431 | A1 * | 9/2016 | Liu | G06K 9/325 |
| 2016/0338407 | A1 * | 11/2016 | Kerdemelidis | A24F 47/008 |
| 2016/0345627 | A1 * | 12/2016 | Liu | A24F 47/008 |
| 2016/0374392 | A1 * | 12/2016 | Liu | H02J 7/0052 392/404 |
| 2016/0374402 | A1 * | 12/2016 | Fernando | A24F 47/008 392/404 |
| 2017/0013882 | A1 * | 1/2017 | Liu | A24F 47/008 |
| 2017/0020191 | A1 * | 1/2017 | Lamb | A24F 47/008 |
| 2017/0135408 | A1 * | 5/2017 | Cameron | A24F 47/008 |
| 2017/0258136 | A1 * | 9/2017 | Hawes | A24F 47/008 |
| 2017/0347704 | A1 * | 12/2017 | Oishi | A24F 47/002 |

FOREIGN PATENT DOCUMENTS

| | | |
|---|---|---|
| EP | 0 516 293 A1 | 2/1992 |
| KR | 10-2012-0098343 A | 9/2012 |
| KR | 10-2012-0113513 A | 10/2012 |
| WO | 2012/134117 A2 | 10/2012 |

OTHER PUBLICATIONS

Written Opinion from corresponding PCT/CN2013/090901 dated Sep. 9, 2014, 3 pages.

* cited by examiner

BATTERY ASSEMBLY AND ATOMIZING ASSEMBLY OF ELECTRONIC CIGARETTE AND ELECTRONIC CIGARETTE

This application is the national phase of International Application No. PCT/CN2013/090901, titled "BATTERY ASSEMBLY AND ATOMIZING ASSEMBLY OF ELECTRONIC CIGARETTE AND ELECTRONIC CIGARETTE", filed on Dec. 30, 2013, which claims the benefit of priority to Chinese patent application No. 201320772413.2, titled "BATTERY ASSEMBLY AND ATOMIZING ASSEMBLY OF ELECTRONIC CIGARETTE AND ELECTRONIC CIGARETTE" and filed with the Chinese State Intellectual Property Office on Nov. 28, 2013, both of which applications are incorporated herein in their entireties by reference thereto.

TECHNICAL FIELD

The present application relates to the technical field of electronic cigarettes, in particular to a battery assembly and an atomizing assembly of an electronic cigarette and an electronic cigarette.

BACKGROUND

Figure 1:
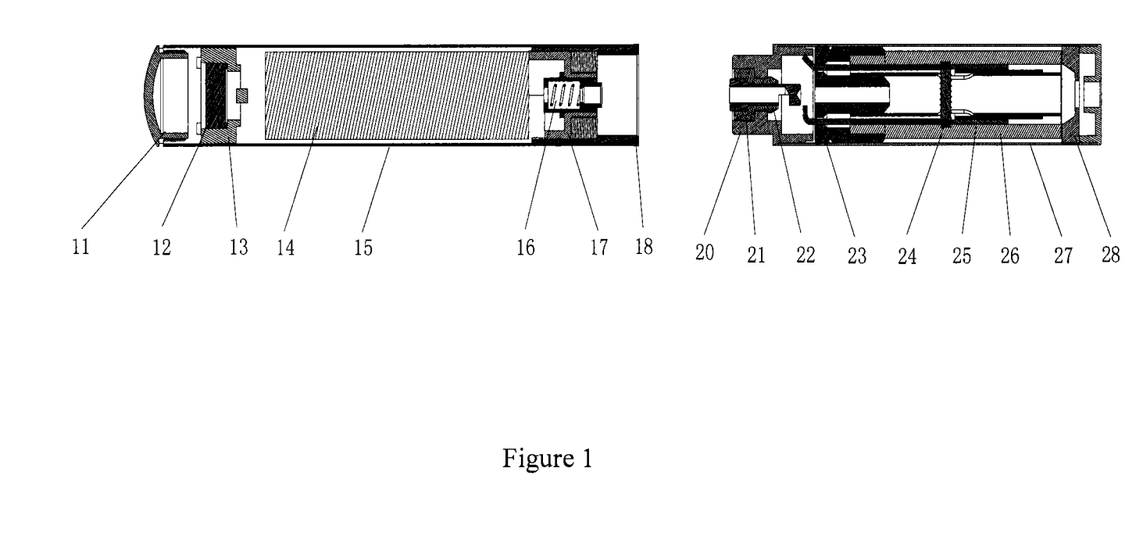
FIG. 1 is a schematic view showing the structure of an electronic cigarette in the conventional technology.

An existing electronic cigarette mainly includes a battery assembly and an atomizing assembly, the structure of which is shown in FIG. 1. The battery assembly includes an end cap 11, a microphone controller 12, a microphone seat 13, a battery 14, a battery sleeve 15, a lower electrode 16, an electrode fixing seat 17 and a connecting seat 18. The atomizing assembly includes a connector 20, an upper electrode 21, an upper insulating ring 22, an atomizing seat 23, an atomizing device 24, a PVC fiberglass sleeving 25, a liquid storage cotton 26, an atomizing sleeve 27 and a mouthpiece cover 28.

In conjunction with FIG. 1, the electronic cigarette can work normally by connecting the connecting seat 18 in the battery assembly to the connector 20 in the atomizing assembly. The inventor found that, the existing electronic cigarettes may be used in combination as long as connectors of the battery assembly and the atomizing assembly can be connected. Thus, when the battery assembly and the atomizing assembly, which are not matched, are used in combination, the power of the heating wire in the atomizing device does not match the power of the battery, thus smoke generated by the atomizing device may have an undesirable smell or in a relatively small quantity, or the atomizing device cannot generate smoke since the heating coil has different resistance value, and damages to the electronic cigarette may be caused, for example battery overheat or battery leakage. In addition, since the existing battery assembly and atomizing assembly can be used in any combination, it is apt to cause the mixed use of cigarette liquids having different flavors and the mixed use of the battery assembly and the atomizing assembly from different manufacturers, which may cause a poor user experience, hinders a user from knowing about the manufacturers and the brands, and is not beneficial for the user to quit smoking.

SUMMARY

In view of this, a battery assembly and an atomizing assembly of an electronic cigarette, and an electronic cigarette are provided according to the present application, which may effectively solve the problem in the conventional technology that an unstable smoke quantity and damages on the electronic cigarette, for example battery overheat or battery leakage, may be caused in a case that the battery assembly and the atomizing assembly, which are not matched, are used in combination.

In order to achieve the above objects, the following technical solutions are provided in the present application.

A battery assembly of an electronic cigarette, configured to form an electronic cigarette in combination with an atomizing assembly, wherein the atomizing assembly is provided with a gas storage chamber configured to store cigarette-liquid odor to be detected, and the battery assembly includes:

- a sensor group arranged on the battery assembly and configured to detect the cigarette-liquid odor to be detected; and
- a microcontroller connected with the sensor group and configured to control a circuit between the battery assembly and the atomizing assembly to be switched on in a case that the microcontroller determines that the cigarette-liquid odor to be detected matches a preset odor information, to enable the electronic cigarette to work normally.

Preferably, the microcontroller includes:

- a pattern recognition device connected with the sensor group and configured to determine composition information of the cigarette-liquid odor to be detected; and
- a control device connected with the pattern recognition device and configured to determine whether the composition information of the cigarette-liquid odor to be detected matches the preset odor information.

Preferably, the sensor group includes at least one gas sensor.

Preferably, the sensor group further includes a temperature sensor.

Preferably, the microcontroller further includes:

- a signal processing device provided between the sensor group and the pattern recognition device, and configured to store the composition information of the cigarette-liquid odor to be detected, and generate a frequency shift signal by performing a frequency shift operation and a correction on a signal indicating the cigarette-liquid odor to be detected, and transmit the frequency shift signal to the pattern recognition device.

Preferably, the battery assembly further includes:

- a notification device electrically connected to the microcontroller and configured to show a matching result from the microprocessor, and the notification device is an alarm or an indicator light.

preferably, the battery assembly further includes:

- a switch provided between the microcontroller and the atomizing assembly and configured to control a power supplying status of the battery assembly.

Preferably, the switch is a key switch or an airflow sensor.

An atomizing assembly of an electronic cigarette is configured to form an electronic cigarette in combination with a battery assembly, and the atomizing assembly is provided with a gas storage chamber configured to store cigarette-liquid odor to be detected.

An electronic cigarette includes a battery assembly and an atomizing assembly, the battery assembly is the battery assembly according to any one of the above technical solutions; and the atomizing assembly is the above atomizing assembly.

According to the above technical solutions, compared with the prior art, a battery assembly of an electronic cigarette according to the present application is configured to form an electronic cigarette in combination with an atomizing assembly. The atomizing assembly is provided with a gas storage chamber configured to store cigarette-liquid odor to be detected. The battery assembly includes a sensor group and a microcontroller. The sensor group is arranged on the battery assembly and configured to detect the cigarette-liquid odor to be detected. The microcontroller is configured to control a circuit between the battery assembly and the atomizing assembly to be switched on in a case that the cigarette-liquid odor to be detected matches the preset odor information, to enable the electronic cigarette to work normally.

Thus, the electronic cigarette has an identification function and can be normally used only when the battery assembly and the atomizing assembly of the electronic cigarette are matched, thereby avoiding the problem that an unstable smoke quantity and damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

DETAILED DESCRIPTION OF THE DRAWINGS

For more clearly illustrating embodiments of the present application or the technical solution in the conventional technology, drawings referred to describe the embodiments or the conventional technology will be briefly described hereinafter. Apparently, the drawings in the following description are only several embodiments of the present application, and for the person skilled in the art other drawings may be obtained based on these drawings without any creative efforts.

| Reference Numbers: | | | |
|---|---|---|---|
| 11 | end cover, | 12 | microphone controller, |
| 13 | microphone seat, | 14 | battery, |
| 15 | battery sleeve, | 16 | lower electrode, |
| 17 | electrode fixing seat, | 18 | connecting seat, |
| 19 | sealing film, | 20 | connector, |

| -continued | | | |
|---|---|---|---|
| Reference Numbers: | | | |
| 21 | upper electrode, | 22 | upper insulating ring, |
| 23 | atomizing seat, | 24 | atomizing device, |
| 25 | PVC fiberglass sleeving, | 26 | liquid storage cotton, |
| 27 | atomizing sleeve, | 28 | mouthpiece cover, |
| 29 | gas storage chamber, | 30 | lower insulating ring, |
| 21a | upper outer electrode, | 21b | upper inner electrode, |
| 16a | lower outer electrode, and | 16b | lower inner electrode. |

DETAILED DESCRIPTION

A battery assembly and an atomizing assembly of an electronic cigarette, and an electronic cigarette are provided according to the present application, wherein the electronic cigarette has an odor identification function to ensure that the electronic cigarette can be normally used only when the battery assembly and the atomizing assembly are matched, thereby avoiding damage to connectors of the electronic cigarette caused by mismatching, and avoiding unnecessary troubles caused by interchange between connectors of electronic cigarettes in different brands.

The technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the protection scope of the present application.

First Embodiment

Figure 2:
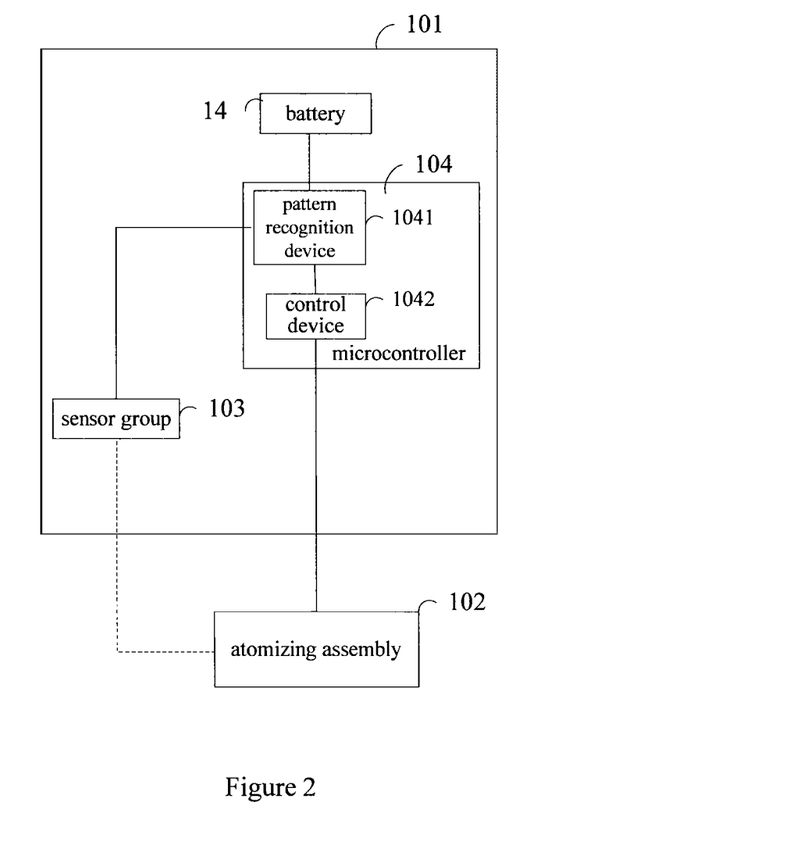
FIG. 2 is a schematic block diagram of an electronic cigarette according to an embodiment of the present application.

Referring to FIG. 2, a battery assembly 101 of an electronic cigarette according to an embodiment of the present application is configured to form an electronic cigarette in combination with an atomizing assembly 102. The atomizing assembly 102 is provided with a gas storage chamber configured to store cigarette-liquid odor to be detected. The battery assembly 101 includes a sensor group 103 and a microcontroller 104.

The sensor group 103 is arranged on the battery assembly and configured to detect the cigarette-liquid odor to be detected. The microcontroller 104 is connected with the sensor group 103 and configured to determine whether the cigarette-liquid odor to be detected matches a preset odor information, and in a case that the cigarette-liquid odor to be detected matches the preset odor information, the microcontroller controls a circuit between the battery assembly and the atomizing assembly to be switched on to enable the electronic cigarette to work normally; and in a case that the cigarette-liquid odor to be detected does not match the preset odor information, the microcontroller controls the circuit between the battery assembly and the atomizing assembly to be switched off to power off the electronic cigarette, that is, the electronic cigarette cannot work at this time.

Thus, the electronic cigarette has an identification function and can be normally used only when the battery assembly and the atomizing assembly of the electronic cigarette are matched, thereby avoiding the problem that an unstable smoke quantity and damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

Preferably, in this embodiment, the microcontroller 104 includes a pattern recognition device 1041 and a control device 1042. The pattern recognition device 1041 is connected with the sensor group 103 and configured to determine composition information of the cigarette-liquid odor to be detected. The control device 1042 is connected with the pattern recognition device and configured to determine whether the composition information of the cigarette-liquid odor to be detected matches the preset odor information. In a case that the composition information of the cigarette-liquid odor to be detected matches the preset odor information, the battery charges the atomizer.

Figure 3:
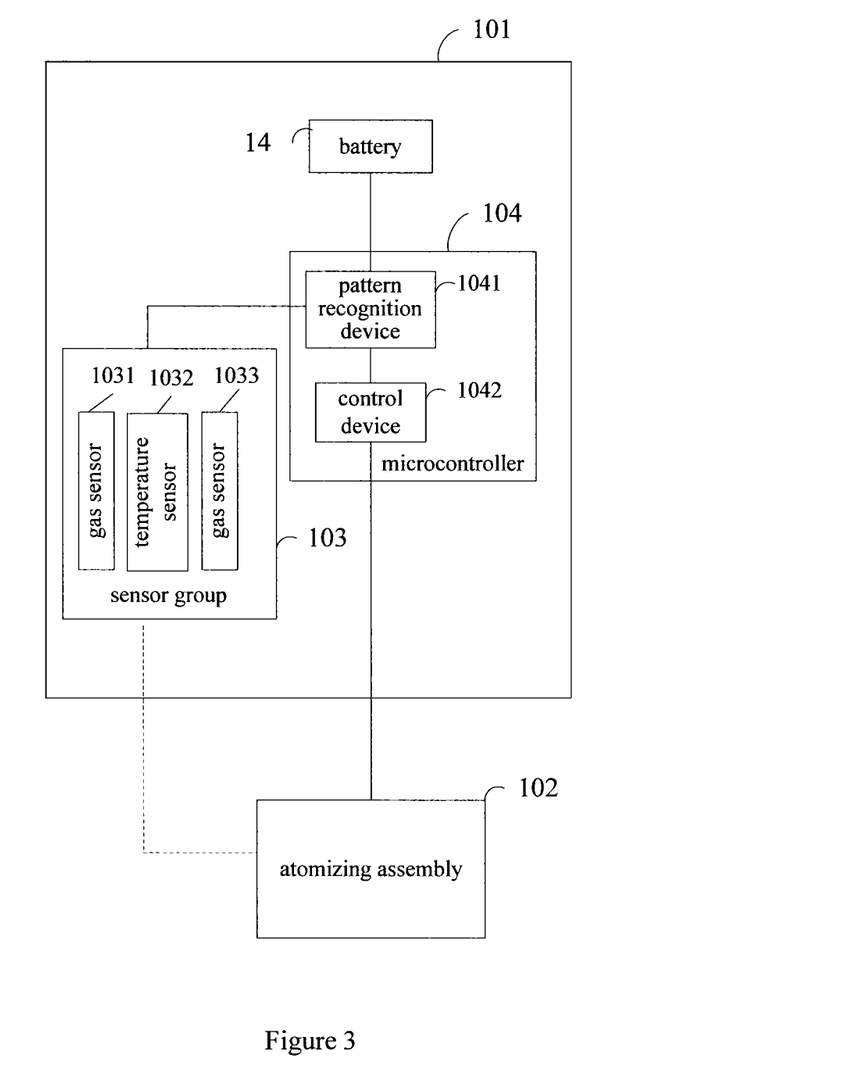
FIG. 3 is a schematic block diagram of an electronic cigarette according to the present application.

Referring to FIG. 3, preferably, the sensor group 103 includes at least one gas sensor 1031, 1033, and may further include a temperature sensor 1032.

Figure 7:
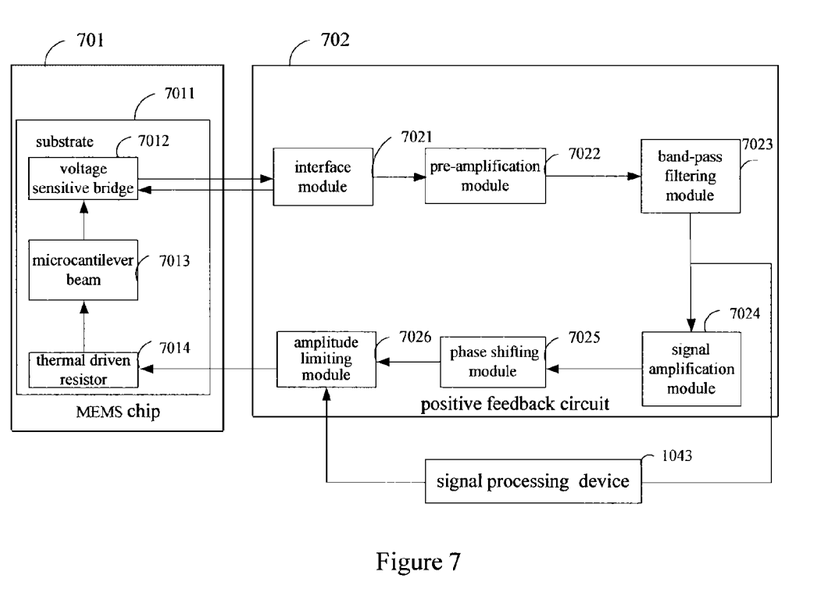
FIG. 7 is a schematic block diagram showing a gas sensor and a signal processing device which are cooperated with each other according to an embodiment of the present application.

The gas sensor is configured to collect a response variable of concentration change of gas compositions in the gas to be detected. The temperature sensor is configured to collect a response variable of temperature change of an environment in which the gas to be detected is located. As shown in FIG. 7, a specific circuit of the gas sensor is provided according to this embodiment.

The gas sensor includes a MEMS chip 701 and a positive feedback circuit 702. The MEMS chip and the positive feedback circuit form a closed-loop self-excited oscillation circuit.

It should be noted that, the MEMS chip is a microcantilever beam mechanical resonator, and a resonant frequency thereof determines a frequency of the closed-loop self-excited oscillation circuit. The MEMS chip includes a substrate, a microcantilever beam, a thermal driven resistor, and a voltage sensitive bridge consisting of several voltage sensitive resistors.

The substrate may be an n-type doping crystal silicon-on-insulator (SOI) wafer. The microcantilever beam may be formed on the SOI substrate by an inductive coupled plasma (ICP) etching process.

The working principle is as follows.

A gas sensitive layer with a certain thickness is provided on a surface of the microcantilever beam of the gas sensor. The material of the gas sensitive layer may employ high molecular polymer, such as polyethylene oxide (PEO) or polyvinyl alcohol (PVA). The gas sensitive layer made of high molecular polymer may be formed by a spraying method, a drop method or a spin-coating method. The method may be selected according to the material of the high molecular polymer layer. The high molecular polymer has respective selective adsorption coefficients for different gas molecules. The vibration frequency of the microcantilever beam changes once gas molecules absorbs on the gas sensitive layer. Each of the gas sensors employs different high molecular polymers and is configured to respond the concentration change of gas compositions in the gas to be detected, that is, to show the concentration change by the change of the vibration frequency of the microcantilever beam.

The thermal driven resistor and the voltage sensitive resistors are all arranged on the microcantilever beam. After the thermal driven resistor is electrified, the microcantilever beam is driven to vibrate. The voltage sensitive bridge is configured to detect the variation frequency of the microcantilever beam and transmit a detected voltage signal to the positive feedback circuit, and a frequency of the detected voltage signal varies with the vibration frequency of the microcantilever beam.

The positive feedback circuit includes an interface module, a pre-amplification module, a band-pass filtering module, a signal amplification module, a phase shifting module, and an amplitude limiting module. In operation, the microcantilever beam is in a resonant vibration state. Gas molecules may be adsorbed on the corresponding gas sensitive layer of the microcantilever beam, thus a mass of the microcantilever beam changes and the resonant frequency of the microcantilever beam changes accordingly. The interface module may detect the variation of the resonant frequency of the microcantilever beam sensed by the voltage sensitive bridge, supply a steady direct-current power supply for the voltage sensitive bridge, and compensate the zero shift of the voltage sensitive bridge by adding a variable resistor. To further describe the operation of the interface module, the voltage sensitive bridge outputs the voltage signal with a frequency varying with the variation frequency of the microcantilever beam to the interface module.

The pre-amplification module includes an AD620 instrumentation amplifier chip, and is configured to amplify the weak voltage signal outputted from the interface module, and then transmit the amplified voltage signal to the band-pass filtering module. The thermal driving is power driving, which may generate a fundamental frequency voltage signal and a double frequency voltage signal. The band-pass filtering module filters the double frequency voltage signal, high frequency noise and low frequency noise, and divides the fundamental frequency voltage signal into two paths, and one path of the fundamental frequency voltage signal functioning as a feedback signal passes through the signal amplification module, the phase shifting module and the amplitude limiting module in sequence and then is transmitted to the thermal driven resistor, and the other path of the fundamental frequency voltage signal functioning as an output signal is transmitted to a signal processing circuit. In this embodiment, the band-pass filter module includes an MAX275 chip.

The signal amplification module includes an OP37 operational amplifier chip which has a high speed, a high precision and a low noise, and is configured to amplify the feedback signal to meet the requirement of the amplitude value of the self-oscillation. The signal amplified by the signal amplification module is inputted to the phase shifting module. The phase shifting module includes an OP37 chip, and is configured to adjust the phase of the feedback signal to meet the requirement of the phase of the self-oscillation. The requirement of the amplitude value of the self-oscillation is that a value of the loop gain is 1, and the requirement of the phase of the self-oscillation is that, with respect to an original signal, the total phase shifting amount of the feedback signal is an integral multiple of $2\pi$.

The amplitude limiting module includes an AD8036AR chip, and is configured to control the amplitude value of the signal fed back to the thermal driven resistor to protect the stability of the circuit and the vibration frequency. The control module controls, by the signal processing circuit, the amplitude limiting module in the gas sensor to select a direct-current bias voltage of the driving signal applied on the thermal driven resistor for the microcantilever beam absorbed with gas molecules, thereby ensuring that the signal generated by the voltage sensitive bridge includes a fundamental frequency voltage signal. The control module may also heat the gas sensitive layer on the microcantilever beam by the thermal driven resistor. A temperature of the gas sensitive layer may be increased by properly increasing the direct-current bias voltage. An adsorption coefficient of the high polymer decreases exponentially as the temperature increases, thus the gas molecules adsorbed in the gas sensitive layer may be excluded quickly, thereby recovering the gas sensitive layer and resetting the gas sensitive layer for the next gas molecule absorbing process. An example is introduced hereinafter to describe the switching of the gas sensor between a normal operation state and an auto recovering state realized by the direct-current bias voltage of the amplitude limiting module.

This embodiment provides two direct-current bias voltages, one direct-current bias voltage is for the normal operation, and the other direct-current bias voltage is configured to increase the temperature of the gas sensitive layer on the microcantilever beam. Gas sensors are connected to the signal processing circuit via parallel ports. The signal processing circuit is configured to input a direct-current bias voltage selection signal sent from the control module to the amplitude limiting module, and the amplitude limiting module is configured to input different direct-current bias voltages with different voltages by a digital alternative switch. A user may switch between the two direct-current bias voltages via the control module according to actual needs.

The signal processing circuit is configured to receive fundamental frequency voltage signals outputted from respective band-pass filtering modules of each gas sensor and each temperature sensor, and store the signals outputted from each gas sensor and each temperature sensor, and then obtain a corrected frequency signal of temperature drift by performing a differential operation, obtain a frequency shift signal by perform a time differential operation on the corrected frequency signal, and then transmit the frequency shift signal to the pattern recognition module. The pattern recognition module is configured to analyze and recognize a pattern formed by the frequency shift signals of all gas sensors, and feed back a recognition result to the control module. In this embodiment, the signal processing circuit includes a PLC16F877 single-chip microcomputer chip.

The odor detection principle of the gas sensor is described hereinabove in detail. The present application may detect the odor based on the above functions of the sensor, and transmit the gas information to the microcontroller to be processed and matched, and to further determine a matching result. If the gas information matches, the battery assembly supplies power to the atomizing assembly.

Figure 4:
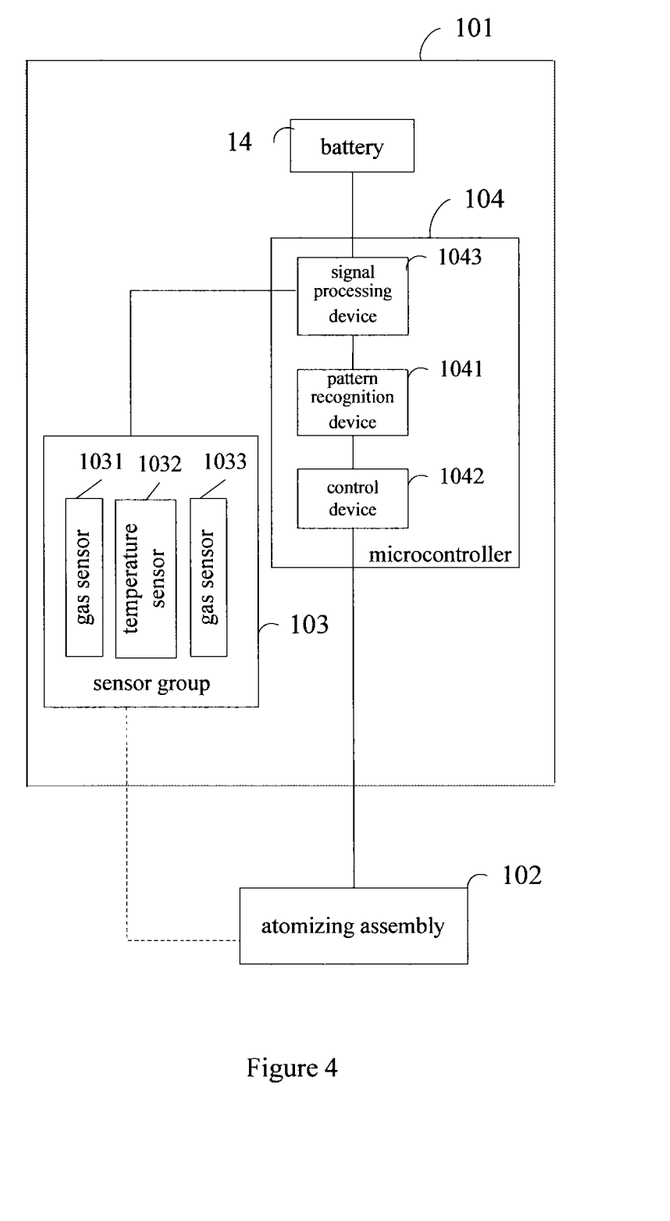
FIG. 4 is a schematic block diagram of another electronic cigarette according to the present application.

Referring to FIG. 4, preferably, the microcontroller according to this embodiment further includes a signal processing device 1043. The signal processing device 1043 is provided between the sensor group and the pattern recognition device, and is configured to store the composition information of the cigarette-liquid odor to be detected, and generate a frequency shift signal by performing a frequency shift operation and a correction on a signal indicating the cigarette-liquid odor to be detected, and transmit the frequency shift signal to the pattern recognition device 1041. In should be noted that, this embodiment may detect a particular odor or several odors of the cigarette liquid, and the odor may be the odor of flavor compositions in the cigarette, such as neophytadiene or solanone, which are not limited herein.

Thus, in a case that the information recognized by the microcontroller does not match the preset information, the circuit between the atomizing assembly and the battery assembly is not switched on, that is, the battery assembly cannot supply power to the atomizing assembly, and the electronic cigarette cannot work normally. In this embodiment, the processor is automatically reset when charging the battery, and it's required to reconnect the atomizing assembly and the battery assembly and recognize the signal again before the electronic cigarette can work normally, thereby preventing the mixed use of atomizing assemblies of different specifications or brands.

Second Embodiment

Figure 5:
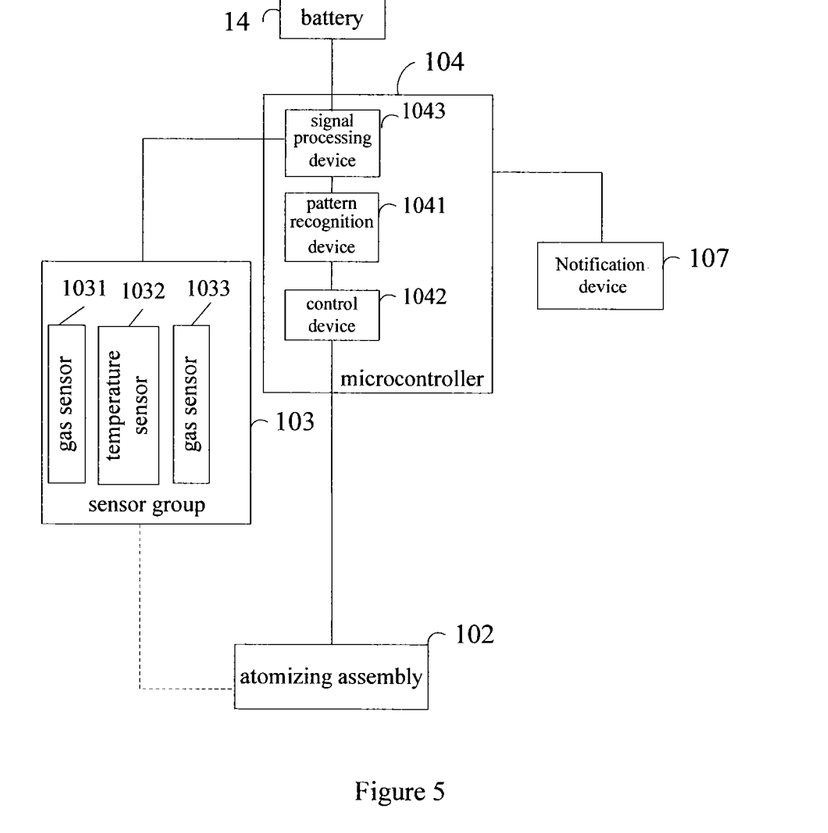
FIG. 5 is a schematic block diagram of another electronic cigarette according to the present application.

Referring to FIG. 5, a battery assembly of an electronic cigarette according to an embodiment of the present application is configured to form an electronic cigarette in combination with an atomizing assembly 102. The battery assembly includes a sensor group 103, a microcontroller 104 and a notification device 107 for notifying identification result. The device is electrically connected to the microprocessor, and is configured to notify the identification result of the microprocessor.

The notification device may be an alarm or an indicator light, and the alarm may be a buzzer alarm, a loudspeaker or the like.

It should be noted that, except for the notifying function, the electronic cigarette in this embodiment has the same working principle as the first embodiment, thus will not be described herein.

Third Embodiment

Figure 6:
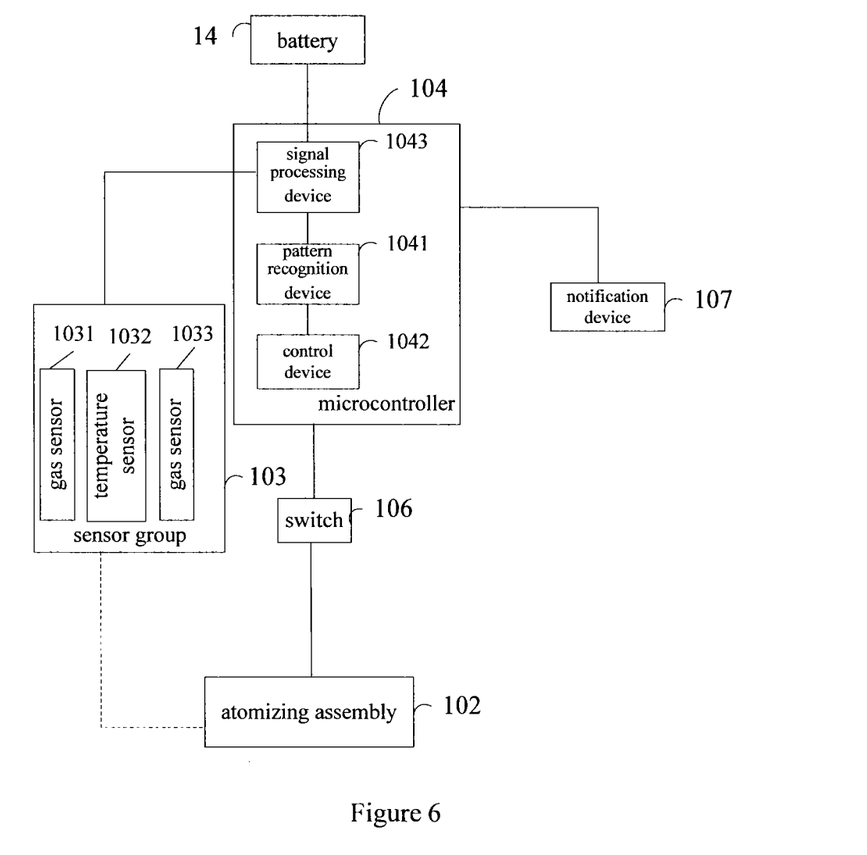
FIG. 6 is a schematic block diagram of another electronic cigarette according to the present application.

Referring to FIG. 6, based on the second embodiment, this embodiment provides another battery assembly of the electronic cigarette, which is configured to form an electronic cigarette in combination with an atomizing assembly 102. The battery assembly includes a sensor group 103, a microcontroller 104 and a switch 106.

The sensor group 103 is configured to detect the cigarette-liquid odor to be detected. The microcontroller 104 is connected with the sensor group 103 and configured to determine whether the cigarette-liquid odor to be detected matches a preset odor information, and in a case that the cigarette-liquid odor to be detected matches the preset odor information, the microcontroller controls a circuit between the battery assembly and the atomizing assembly to be switched on, and the switch 106 is switched on to enable the electronic cigarette to work normally; and in a case that the cigarette-liquid odor to be detected does not match the preset odor information, the microcontroller controls the circuit between the battery assembly and the atomizing assembly to be switched off to power off the electronic cigarette, that is, the electronic cigarette cannot work normally.

It should be noted that, the switch 106 may be an airflow sensor or a switch having mechanical button. In a case that the switch 106 is an airflow sensor, the switch 106 is provided in an airflow channel communicated with an atomizing channel of the atomizing assembly. During smoking, the airflow sensor is triggered by the airflow and transmits a smoking signal to the control device 1042, and the control device 1042 controls the battery to supply power to the atomizing assembly.

Thus, the electronic cigarette has an identification function and can be normally used only when the battery assembly and the atomizing assembly of the electronic cigarette are matched, thereby avoiding the problem that an unstable smoke quantity and damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

Fourth Embodiment

Figure 8:
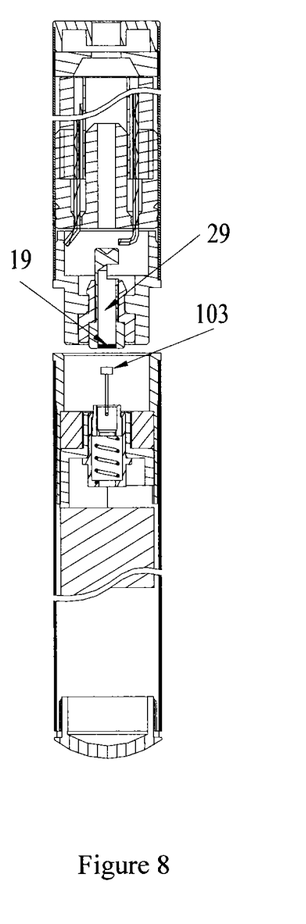
FIG. 8 is a schematic view showing the structure of an electronic cigarette according to an embodiment of the present application.

Referring to FIG. 8, in addition to the above embodiments, this embodiment provides an atomizing assembly of the electronic cigarette. The atomizing assembly is provided with a gas storage chamber 29 configured to store cigarette-liquid odor to be detected. The gas storage chamber 29 is located at one end of the atomizing assembly 102, and an end surface of the atomizing assembly 102 is provided with a sealing film 19 configured to seal the gas storage chamber 29. Preferably, the cigarette-liquid odor in the gas storage chamber 29 is the same as that of the cigarette liquid in the atomizing assembly to be atomized. Apparently, the cigarette-liquid odor in the gas storage chamber 29 may be different from that of the cigarette liquid in the atomizing assembly to be atomized, as long as the cigarette-liquid odor in the gas storage chamber 29 may indicate the atomizing assembly. In a case that the battery assembly and the atomizing assembly are connected, the sensor group 103 passes through the sealing film 19 and extends into the gas storage chamber 29.

According to this embodiment, an electronic cigarette may be formed by combining the atomizing assembly and the battery assembly. An electronic cigarette, including a battery assembly and an atomizing assembly, is further provided in this embodiment. The battery assembly includes the microcontroller and the sensor group according to any one of the above embodiments. A lower electrode of the atomizing assembly is provided with a gas storage chamber configured to store the cigarette-liquid odor to be detected.

Reference is made to FIG. 8, which is a schematic view showing the installation position of the sensor group and the microcontroller according to this embodiment. Apparently, the position thereof are not limited to this, and the description herein is only exemplary.

The atomizing assembly is provided with a gas storage chamber 29, and correspondingly, the battery assembly is provided with a sensor group 103. It could be understood that, in a case that the sensor group 103 can extend into the cigarette liquid atomizing channel in the atomizing assembly, it is not necessary to provide an independent gas storage chamber 29.

In conclusion, a battery assembly of an electronic cigarette according to the present application is configured to form an electronic cigarette in combination with an atomizing assembly. The atomizing assembly is provided with a gas storage chamber configured to store cigarette-liquid odor to be detected. The battery assembly includes a sensor group and a microcontroller. The sensor group is arranged on the battery assembly and configured to detect the cigarette-liquid odor to be detected. The microcontroller is configured to control a circuit between the battery assembly and the atomizing assembly to be switched on in a case that the cigarette-liquid odor to be detected matches the preset odor information, to enable the electronic cigarette to work normally.

Thus, the electronic cigarette has an identification function and can be normally used only when the battery assembly and the atomizing assembly of the electronic cigarette are matched, thereby avoiding the problem that an unstable smoke quantity and damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of cigarette liquids having different flavors, and the mixed use of the battery assembly and the atomizing assembly from different manufacturers.

The above embodiments are described in a progressive manner. Each of the embodiments is mainly focused on describing its differences from other embodiments, and references may be made among these embodiments with respect to the same or similar portions among these embodiments. For the device in the embodiments, the description thereof is relatively simpler since it is corresponding to the method disclosed in the embodiments, hence, related parts of the device can refer to the description of the method.

Based on the above description of the disclosed embodiments, the person skilled in the art is capable of carrying out or using the present application. It is obvious for the person skilled in the art to make many modifications to these embodiments. The general principle defined herein may be applied to other embodiments without departing from the spirit or scope of the present application. Therefore, the present application is not limited to the embodiments illustrated herein, but should be defined by the broadest scope consistent with the principle and novel features disclosed herein.

What is claimed is:

1. A battery assembly of an electronic cigarette, configured to form the electronic cigarette in combination with an atomizing assembly, wherein the atomizing assembly is provided with a gas storage chamber configured to store cigarette-liquid odor to be detected, and the battery assembly comprises:
   a sensor group arranged on the battery assembly and configured to detect the cigarette-liquid odor to be detected; and
   a microcontroller electrically connected with the sensor group and configured to control a circuit between the battery assembly and the atomizing assembly to be switched on in a case that the microcontroller determines that the cigarette-liquid odor to be detected matches a preset odor information, to enable the electronic cigarette to work normally.

2. The battery assembly according to claim 1, wherein the microcontroller comprises:
   a pattern recognition device electrically connected with the sensor group and configured to determine composition information of the cigarette-liquid odor to be detected; and
   a control device electrically connected with the pattern recognition device and configured to determine whether the composition information of the cigarette-liquid odor to be detected matches the preset odor information.

3. The battery assembly according to claim 1, wherein the sensor group comprises at least one gas sensor.

4. The battery assembly according to claim 3, wherein the sensor group further comprises a temperature sensor.

5. The battery assembly according to claim 2, wherein the microcontroller further comprises:
   a signal processing device provided between the sensor group and the pattern recognition device and electrically connected with the sensor group and the pattern recognition device, and configured to store the composition information of the cigarette-liquid odor to be detected, and generate a frequency shift signal by performing a frequency shift operation and a correction on a signal indicating the cigarette-liquid odor to be detected, and transmit the frequency shift signal to the pattern recognition device.

6. The battery assembly according to claim 1, wherein the battery assembly further comprises:
a notification device electrically connected to the microcontroller and configured to show a matching result from the microcontroller, and the notification device is an alarm or an indicator light.

7. The battery assembly according to claim 1, wherein the battery assembly further comprises:
a switch provided between the microcontroller and the atomizing assembly, electrically connected with the microcontroller and the atomizing assembly and configured to control a power supplying status of the battery assembly.

8. The battery assembly of the electronic cigarette according to claim 7, wherein the switch is a key switch or an airflow sensor.

9. An electronic cigarette, comprising a battery assembly and an atomizing assembly, wherein the atomizing assembly is provided with a gas storage chamber configured to store cigarette-liquid odor to be detected, and the battery assembly comprises:
a sensor group arranged on the battery assembly and configured to detect the cigarette-liquid odor to be detected; and
a microcontroller electrically connected with the sensor group and configured to control a circuit between the battery assembly and the atomizing assembly to be switched on in a case that the microcontroller determines that the cigarette-liquid odor to be detected matches a preset odor information, to enable the electronic cigarette to work normally.

10. The electronic cigarette according to claim 9, wherein the microcontroller comprises:
a pattern recognition device electrically connected with the sensor group and configured to determine composition information of the cigarette-liquid odor to be detected; and
a control device electrically connected with the pattern recognition device and configured to determine whether the composition information of the cigarette-liquid odor to be detected matches the preset odor information.

11. The electronic cigarette according to claim 9, wherein the sensor group comprises at least one gas sensor.

12. The electronic cigarette according to claim 11, wherein the sensor group further comprises a temperature sensor.

13. The electronic cigarette according to claim 10, wherein the microcontroller further comprises:
a signal processing device provided between the sensor group and the pattern recognition device and electrically connected with the sensor group and the pattern recognition device, and configured to store the composition information of the cigarette-liquid odor to be detected, and generate a frequency shift signal by performing a frequency shift operation and a correction on a signal indicating the cigarette-liquid odor to be detected, and transmit the frequency shift signal to the pattern recognition device.

14. The electronic cigarette according to claim 9, wherein the battery assembly further comprises:
a notification device electrically connected to the microcontroller and configured to show a matching result from the microcontroller, and the notification device is an alarm or an indicator light.

15. The electronic cigarette according to claim 9, wherein the battery assembly further comprises:
a switch provided between the microcontroller and the atomizing assembly, electrically connected with the microcontroller and the atomizing assembly and configured to control a power supplying status of the battery assembly.

16. The electronic cigarette according to claim 15, wherein the switch is a key switch or an airflow sensor.

17. A method for determining compatibility of a battery assembly with an atomizing assembly, the battery assembly and the atomizing assembly being configured to form an electronic cigarette, the atomizing assembly having a gas storage chamber configured to store cigarette-liquid odor to be detected, and the method comprises:
detecting the cigarette-liquid odor to be detected by a sensor group arranged on the battery assembly;
determining, by a microcontroller electrically connected with the sensor group, whether the cigarette-liquid odor to be detected matches a preset odor information; and
controlling, by the microcontroller, a circuit between the battery assembly and the atomizing assembly to be switched on in a case that the microcontroller determines that the cigarette-liquid odor to be detected matches the preset odor information, to enable the electronic cigarette to work normally.

18. The method according to claim 17, wherein determining, by a microcontroller electrically connected with the sensor group, whether the cigarette-liquid odor to be detected matches a preset odor information comprises:
determining composition information of the cigarette-liquid odor to be detected by a pattern recognition device electrically connected with the sensor group; and
determining, by a control device electrically connected with the pattern recognition device, whether the composition information of the cigarette-liquid odor to be detected matches the preset odor information.

19. The method according to claim 18, wherein before determining composition information of the cigarette-liquid odor to be detected by a pattern recognition device electrically connected with the sensor group, the method further comprises:
storing composition information of the cigarette-liquid odor to be detected by a signal processing device provided between the sensor group and the pattern recognition device and electrically connected with the sensor group and the pattern recognition device;
generating, by the signal processing device, a frequency shift signal by performing a frequency shift operation and a correction on a signal indicating the cigarette-liquid odor to be detected; and
transmitting the frequency shift signal to the pattern recognition device by the signal processing device.

20. The method according to claim 17, further comprising:
showing a matching result from the microcontroller by a notification device electrically connected to the microcontroller.

* * * * *